US009126997B1

(12) United States Patent
Budunova et al.

(10) Patent No.: US 9,126,997 B1
(45) Date of Patent: Sep. 8, 2015

(54) SYNERGISTIC EFFECT OF GLUCOCORTICOID RECEPTOR AGONISTS IN COMBINATION WITH PROTEOSOME INHIBITORS FOR TREATING LEUKEMIA AND MYELOMA

(75) Inventors: Irina Budunova, Chicago, IL (US); Alexander Yemelyanov, Wheeling, IL (US)

(73) Assignee: Northwestern University, Evanston, IL (US)

( * ) Notice: Subject to any disclaimer, the term of this patent is extended or adjusted under 35 U.S.C. 154(b) by 820 days.

(21) Appl. No.: 13/226,865

(22) Filed: Sep. 7, 2011

Related U.S. Application Data

(60) Provisional application No. 61/380,601, filed on Sep. 7, 2010.

(51) Int. Cl.
C07D 471/02 (2006.01)
C07D 271/00 (2006.01)
A01N 43/42 (2006.01)

(52) U.S. Cl.
CPC .............. *C07D 471/02* (2013.01); *A01N 43/42* (2013.01); *C07D 271/00* (2013.01)

(58) Field of Classification Search
CPC ..... C07D 471/02; C07D 271/00; A01N 43/42
USPC .................................... 546/113, 18; 514/300
See application file for complete search history.

(56) References Cited

U.S. PATENT DOCUMENTS

| | | | |
|---|---|---|---|
| 5,780,454 A | 7/1998 | Adams et al. | |
| 6,083,903 A | 7/2000 | Adams et al. | |
| 6,297,217 B1 | 10/2001 | Adams et al. | |
| 6,617,317 B1 | 9/2003 | Adams et al. | |
| 6,713,446 B2 | 3/2004 | Gupta | |
| 6,838,477 B2 | 1/2005 | Schreiber et al. | |
| 6,849,743 B2 | 2/2005 | Soucy et al. | |
| 6,958,319 B2 | 10/2005 | Gupta | |
| 7,119,080 B2 | 10/2006 | Adams | |
| 7,223,745 B2 | 5/2007 | Chatterjee et al. | |
| 7,232,818 B2 | 6/2007 | Smyth et al. | |
| 2003/0232823 A1* | 12/2003 | Betageri et al. | 514/230.5 |
| 2004/0138153 A1* | 7/2004 | Ramesh et al. | 514/43 |
| 2005/0245435 A1 | 11/2005 | Smyth et al. | |
| 2007/0161693 A1 | 7/2007 | Corey | |

FOREIGN PATENT DOCUMENTS

| | | |
|---|---|---|
| WO | 02094311 | 11/2002 |
| WO | 03033506 | 4/2003 |
| WO | 03033507 | 4/2003 |
| WO | 03059898 | 7/2003 |
| WO | 03084551 | 10/2003 |
| WO | 03101481 | 12/2003 |
| WO | 2004004749 | 1/2004 |
| WO | 2004011019 | 2/2004 |
| WO | 2004014882 | 2/2004 |
| WO | 2004012732 | 5/2004 |
| WO | 2004064755 | 8/2004 |
| WO | 2004071382 | 8/2004 |
| WO | 2004073624 | 9/2004 |
| WO | 2005002572 | 1/2005 |
| WO | 2005014783 | 2/2005 |
| WO | 2005061530 | 7/2005 |
| WO | 2005094423 | 10/2005 |
| WO | 2005099687 | 10/2005 |
| WO | 2005105826 | 11/2005 |
| WO | 2006017981 | 2/2006 |
| WO | 2006060809 | 6/2006 |
| WO | 2006086600 | 8/2006 |

OTHER PUBLICATIONS

Lesovaya et al., "Combination of a selective activator of the glucocorticoid receptor Comppound A with a proteasome inhibitor as a novel strategy for chemotherapy of hematologic malignancies", Cell Cycle, Jan. 1, 2013, 12(1):133-144.
Coghlan et al., "A novel antiinflammatory maintains glucocorticoid efficacy with reduced side effects", Molecular Endocrinology, 2003, 17(5):860-869.
Guedat et al., "Patented small molecule inhibitors in the ubiquitin proteasome system", BMC Biochemistry, 2007, 8(Suppl. I):S14.
Kinyamu et al., "Estrogen receptor-dependent proteasomal degradation of the glucocorticoid receptor is coupled to an increase in Mdm2 protein expression", Molecular and Cellular Biology, Aug. 2003, 23(16):5867-5881.
Kinyamu et al., "Linking the ubiquitin-proteasome pathway to chromatin remodeling/modification by nuclear receptors", Journal of Molecular Endocrinology, 2005, 34:281-297.
Lin et al., "trans-Activation and repression properties of the novel nonsteroid glucocorticoid receptor ligand 2,5-Dihydro-9-hydroxy-10-methoxy-2,2,4-trimethyl-5-(1-methylcyclohexen-3-y1)-1H[1]benzopyrano[3,4-f]quinoline (A276575) and its four stereoisomers", Molecular Pharmacology, 2002, 62(2):297-303.
Newton et al., "Separating transrepression and transactivation: a distressing divorce for the glucocorticoid receptor?", Molecular Pharmacology, 2007, 72(4):799-809.
Reichardt et al., "DNA binding of the glucocorticoid receptor is not essential for survival", Cell, May 15, 1998, 93:531-541.
Rhen et al., "Antiinflammatory action of glucocorticoids—new mechanisms for old drugs", The New England Journal of Medicine, Oct. 20, 2005, 353(16):1711.
Schacke et al., "Dissociation of transactivation from transrepression by a selective glucocorticoid receptor agonist leads to separation of therapeutic effects from side effects", PNAS, Jan. 6, 2004, 101(1):227-232.

(Continued)

*Primary Examiner* — David Lukton
(74) *Attorney, Agent, or Firm* — Andrus Intellectual Property Law, LLP

(57) ABSTRACT

Disclosed are methods and pharmaceutical compositions for treating diseases, disorders, and conditions associated with glucocorticoid receptor (GR) expression and activity. The disclosed methods typically include administering to a patient in need thereof a proteasome inhibitor and administering to the patient in need thereof a glucocorticoid receptor (GR) agonist, either before, concurrently with, or after the proteasome inhibitor is administered.

20 Claims, No Drawings

(56) References Cited

OTHER PUBLICATIONS

Schacke et al., "Insight into the molecular mechanisms of glucocorticoid receptor action promotes identification of novel ligands with an improved therapeutic index", Experimental Dermatology, 2006, 15:565-573.

Vayssiere et al., "Synthetic glucocorticoids that dissociate transactivation and AP-1 transrepression exhibit antiinflammatory activity in vivo", Molecular Endocrinology, 1997, 11:1245-1255.

Wallace et al., "Proteasome-mediated glucocorticoid receptor degradation restricts transcriptional signaling by glucocorticoids", Journal of Biological Chemistry, Nov. 16, 2001, 276(46):42714-42721.

Zhang et al., "BOL-303242-X, a novel selective glucocorticoid receptor agonist, with full anti-inflammatory properties in human ocular cells", Molecular Vision, 2009, 15:2606-2616.

\* cited by examiner

SYNERGISTIC EFFECT OF GLUCOCORTICOID RECEPTOR AGONISTS IN COMBINATION WITH PROTEOSOME INHIBITORS FOR TREATING LEUKEMIA AND MYELOMA

CROSS-REFERENCE TO RELATED APPLICATIONS

The present application claims the benefit under 35 U.S.C. 119(e) to U.S. Provisional Patent Application No. 61/380,601, filed on Sep. 7, 2010, the contents of which are incorporated herein by reference in their entirety.

STATEMENT REGARDING FEDERALLY SPONSORED RESEARCH OR DEVELOPMENT

This invention was made with government support under grant number R01 CA118890 awarded by the National Institutes of Health. The government has certain rights in the invention.

BACKGROUND

The field of the invention relates to methods for treating diseases and disorders associated with glucocorticoid receptor (GR) activity.

Glucocorticoid receptors (GR) are observed transcription factors that regulate gene expression. In non-activated cells, each receptor resides in the cytoplasm in a complex with chaperone proteins. Upon activation by a GR agonist, the GRs dissociate from the chaperones, form homo-dimers, and enter the nucleus where they interact with the regulatory sequences in gene promoters.

Glucocorticoid hormones are a mainstay of therapy of numerous hyperproliferative and inflammatory diseases including asthma, arthritis, psoriasis, dermatitis and others. They are also major component of chemotherapy of numerous blood cancers including acute childhood leukemia and multiple myeloma. However, some patients are initially resistant to glucocorticoids and most patients chronically treated with topical or systemic glucocorticoids develop resistance to these steroids (i.e., tachyphylaxis).

The biological effects of glucocorticoids are mediated by the glucocorticoid receptor (GR), a transcription factor that regulates gene expression via (i) DNA-dependent transactivation that requires GR dimerization and binding of GR dimer to gene promoters and (ii) DNA-independent transrepression mediated via negative interaction between the GR monomer and other transcription factors. While GR transrepression is the leading mechanism of anti-inflammatory and anti-proliferative effects of glucocorticoids, many metabolic side effects are mediated by GR transactivation. Thus, selective GR activators (called SEGRA) have been designed to prevent GR dimerization and to specifically shift GR activity towards GR transrepression. In preclinical studies SEGRA showed improved therapeutic index compared to glucocorticoids, hence holding a great potential for the treatment of patients.

The sensitivity to glucocorticoids directly depends on the amount of functional GR protein in cells. The 26S proteasome, a proteolytic complex that regulates the concentration of many cellular proteins, plays a central role in the regulation of GR protein stability. Proteasomes also are responsible for cell desensitization to glucocorticoids via accelerated hormone-induced GR degradation after treatment. This GR autodown regulation is viewed as one of the important mechanisms for the development of acquired resistance to glucocorticoids in the clinic.

SUMMARY

Disclosed are methods and pharmaceutical compositions for treating or preventing diseases, disorders, and conditions associated with glucocorticoid receptor (GR) activities. The diseases, disorders and conditions treated or prevented by the methods disclosed herein typically are responsive to modulation of GR activities.

In some embodiments, the disclosed methods include administering to a patient in need thereof a proteasome inhibitor and administering to the patient in need thereof a glucocorticoid receptor (GR) agonist. The proteasome inhibitor may be administered before, concurrently with, or after the GR agonist is administered.

Typically, the patient is administered an effective amount of the proteasome inhibitor for elevating GR levels in the patient. For example, the effective amount of the proteasome inhibitor may elevate GR protein levels in epithelia or lymphoid cells of the patient.

Typically, the patient is administered an effective amount of the GR agonist. For example, the effective amount of the GR agonist may result in transactivation or preferably transrepression of responsive genes in cells of the patient (e.g., in epithelial or lymphoid cells).

The patient may be administered an effective amount of the proteasome inhibitor before, concurrently with, or after the effective amount of the GR agonist. In some embodiments, the patient has previously been administered a GR agonist and is exhibiting tachyphylaxis to GR agonist therapy. In other embodiments, the patient has not previously been administered a GR agonist and the method prevents tachyphylaxis to GR agonist therapy in the patient.

Suitable patients for the methods disclosed herein may include a patient having or at risk for developing an inflammatory disease or disorder, which may include but is not limited to asthma, arthritis, psoriasis, and dermatitis. Suitable patients for the methods disclosed herein also may include a patient having or at risk for developing a cell hyperproliferative disease or disorder, which may include but is not limited to leukemia and myeloma.

Suitable proteasome inhibitors for use in the methods disclosed herein may include but are not limited to peptide boronic acid compounds, NPI-0052 (salinosporamide A analogs), 2-pyrrolidone compounds, epigallocatechin 3-gallate (EGCG) analogs (in particular those analogs that are specific for proteasome inhibition), PR-171, epoxomycin analogs, peptide analogs, tetrapeptide derivatives, tyropeptide A analogs, and combinations thereof. In some embodiments, the proteasome inhibitor inhibits one or more enzymatic activities of a proteasome selected from β1 subunit activity (chymotryptic-like activity), β2 subunit activity (tryptic-like activity), and β5 subunit activity (post-glutamyl peptidyl hydrolytic-like activity). One suitable proteasome inhibitor is bortezomib (BZ) or a pharmaceutically acceptable salt thereof, which for example, may be administered to a patient at a dosage of about of about 0.7 mg/m to about 1.9 mg/m$^2$. Preferably, the proteasome inhibitor selectively inhibits proteasome activity.

Suitable GR agonists may include selective GR agonists (SEGRA). Suitable SEGRAs may include, but are not limited to, BOL-303242-X, A 276575, RU 24858, and octahydrophenanthrene-2,7-diol derivatives. Other suitable SEGRAs may include any of the following compounds (L-IX):

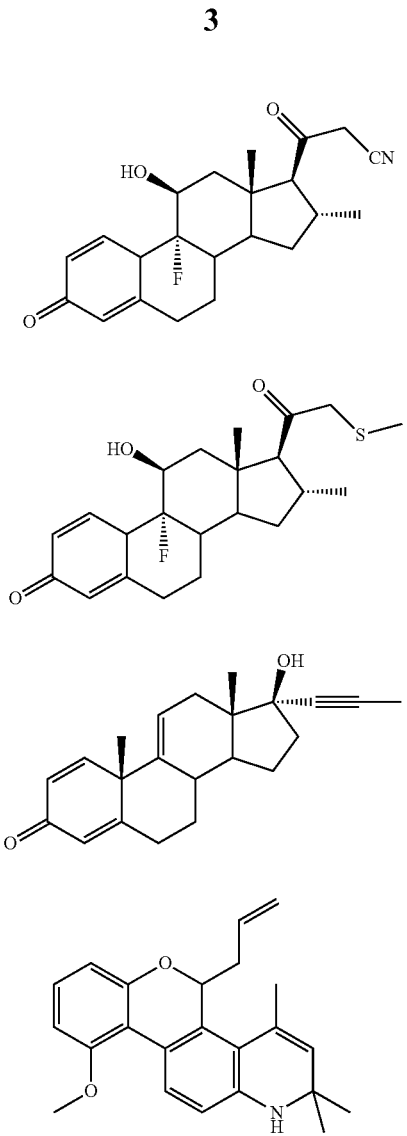
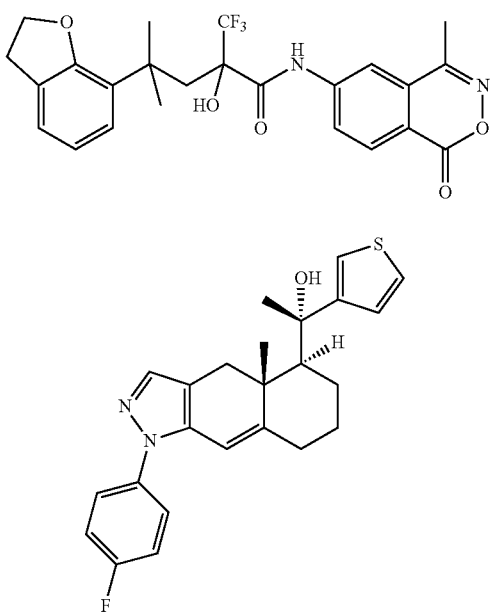
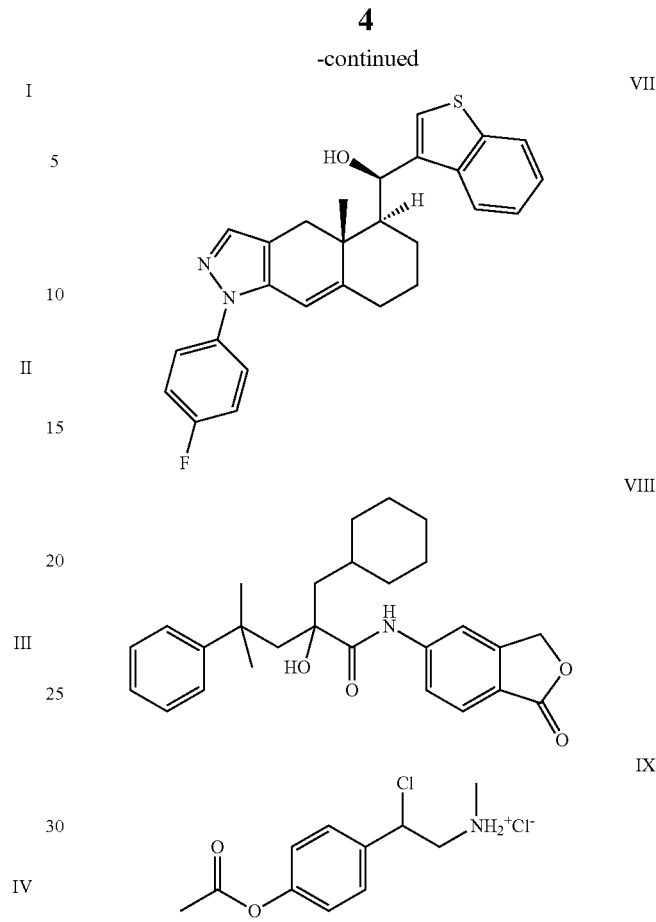

Also contemplated herein are pharmaceutical compositions and kits. The compositions and kits may include a combination of a proteasome inhibitor and a GR agonist as contemplated herein (e.g., bortezomib or a pharmaceutically acceptable salt thereof in combination with a SEGRA).

DETAILED DESCRIPTION

The present invention is described herein using several definitions, as set forth below and throughout the application.

Unless otherwise specified or indicated by context, the terms "a", "an", and "the" mean "one or more." For example, "a proteasome inhibitor" should be interpreted to mean "one or more proteasome inhibitors." Similarly, "a GR agonist" should be interpreted to mean "one or more GR agonists."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used. "about" and "approximately" will mean plus or minus ≤10% of the particular term and "substantially" and "significantly" will mean plus or minus ≥10% of the particular term.

As used herein, the terms "include" and "including" have the same meaning as the terms "comprise" and "comprising." For example, a "pharmaceutical composition that includes a compound" should be interpreted to mean "a pharmaceutical composition that comprises a compound."

The compounds and compositions disclosed herein may modulate GR expression (e.g., expression of the GR protein), and/or the compounds and compositions disclosed herein may modulate GR activity. Glucocorticoid receptor activity may include one or more of ligand binding, transactivation of target genes, and transrepression of target genes.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, a "patient" may be interchangeable with "subject" or "individual" and means an animal, which may be a human or non-human animal, in need of treatment. Non-human animals may include dogs, cats, horses, cows, pigs, sheep, and the like.

A "patient in need thereof" may include a patient having a disease, disorder, or condition that is responsive to modulation of GR expression or GR activity. Modulation may include induction of activity or inhibition of activity. For example, a "patient in need thereof" may include a patient having a disease, disorder, or condition that is responsive to a treatment method that includes induction of GR protein expression or induction of GR transrepression activity.

A "patient in need thereof" may include a patient exhibiting or at risk for developing tachyphylaxis. As utilized herein, "tachyphylaxis" is defined as a rapid decrease in response to a drug after repeated dosages over a period of time, such that increasing the dose of the drug does not increase the pharmacological response. For example, a "patient in need thereof" may include a patient exhibiting or at risk for developing tachyphylaxis associated with GR agonist therapy where the patient exhibits a rapid decrease in response to a GR agonist after repeated dosages over a period of time, such that increasing the dose of the GR agonist does not increase the pharmacological response in the patient. A "patient in need thereof" may include a patient in need of increased GR protein expression (e.g., a patient exhibiting decreased GR protein expression after having been treated with a GR agonist).

A "patient in need thereof" may include a patient having or at risk for developing an inflammatory disease or disorder. A patient having or at risk for developing an inflammatory disease or disorder may include a patient having or at risk for developing asthma, arthritis, psoriasis, and dermatitis.

A "patient in need thereof" may include a patient having or at risk for developing a cell proliferative disease or disorder. A patient having or at risk for developing a cell proliferative disease or disorder may include a patient having or at risk for developing a cancer, for example, a blood cancer such as leukemia or myeloma.

The disclosed methods typically include administering an effective amount of a proteasome inhibitor. "Proteasome inhibitors" may include, for example, peptide boronic acid compounds, NP-0052 (salinosporamide A analogs), 2-pyrrolidone compounds, epigallocatechin 3-gallate (EGCG) analogs (in particular those analogs that are specific for proteasome inhibition), PR-171, epoxomycin analogs, peptide analogs, tetrapeptide derivatives, tyropeptide A analogs, and combinations thereof. The proteasome inhibitor preferably inhibits one or more enzymatic activities of a proteasome selected from β1 subunit activity (chymotryptic-like activity), β2 subunit activity (tryptic-like activity), and β5 subunit activity (post-glutamyl peptidyl hydrolytic-like activity). In some embodiments, the proteasome inhibitor is a peptide boronic acid compound or a pharmaceutically acceptable salt thereof that reversibly inhibits subunit β1 activity of the proteasome.

Proteasome inhibitors are known in the art. For example, proteasome inhibitors are described in U.S. Pat. Nos. 7,232,818; 7,223,745; 7,119,080; 6,958,319, 6,849,743; 6,838,477; 6,713,446; 6,617,317; 6,297,217; 6,083,903; and 5,780,454 (all of which are incorporated by reference herein in their entireties); U.S. Published Application Nos. 2007/0161693 and 2005/0245435 (which are incorporated by reference herein in their entireties); Published International Application Nos. WO03033507; WO03033506; WO2006086600; WO2004064755; WO2006060809; WO2005002572; WO2005099687; WO2004071382; WO2006017981; WO03059898; WO2005094423; WO2005061530; WO2004014882; WO2005105826; WO2005014783; WO03101481; WO2004073624; WO2004012732; WO2004011019; WO02094311; WO2004004749; and WO03084551 (all of which are incorporated by reference herein in their entireties); and scientific review articles, e.g., "Patented small molecule inhibitors of the ubiquitin proteasome system," Philippe Guédat and Frédéric Colland, BMC Biochemistry 2007, 8(Suppl I):S14 (incorporated by reference herein in its entirety).

In some embodiments of the disclosed methods, suitable proteasome inhibitors may include compounds having a formula:

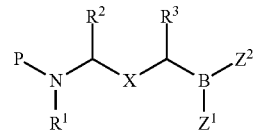

or a pharmaceutically acceptable salt thereof, where
P is $R^7$—C(O)— or —$SO_2$—, where $R^7$ is pyrazinyl (e.g., where P is 2-pyrazinecarbonyl);
X is —C(O)—NH—;
$R^1$ is hydrogen or alkyl (e.g., where $R^1$ is hydrogen);
$R^2$ and $R^3$ are independently hydrogen, branched or straight chain alkyl (e.g., $C_{1-12}$ alkyl), cycloalkyl (e.g., $C_{3-10}$ cycloalkyl), aryl (e.g., $C_{6-10}$ aryl) or
—$CH_2$—$R^5$;
$R^5$, in each instance, is one of aryl, aralky, alkaryl, cycloalky, or —W—$R^6$, where W is chalcogen and $R^6$ is alkyl (e.g., where $R^5$, in each instance, is one of $C_{6-10}$ aryl, $C_{6-10}$ ar($C_{1-6}$) alkyl, $C_{1-6}$ alk($C_{6-10}$)aryl, $C_{3-10}$ cycloalkyl, $C_{1-8}$ alkoxy, or $C_{1-8}$ alkylthio);
where the ring portion of any of said aryl, aralkyl, or alkaryl in $R^2$, $R^3$ and $R^5$ can be optionally substituted by one or two substituents independently selected from the group consisting of $C_{1-6}$ alkyl, $C_{3-8}$ cycloalkyl, $C_{1-6}$ alkyl($C_{3-8}$)cycloalkyl, $C_{2-8}$ alkenyl, $C_{2-8}$ alkynyl, cyano, amino, $C_{1-6}$ alkylamino, di($C_{1-6}$)alkylamino, benzylamino, dibenzylamino, nitro, carboxy, carbo($C_{1-6}$)alkoxy, trifluoromethyl, halogen, $C_{1-6}$ alkoxy, $C_{6-10}$ aryl, $C_{6-10}$ aryl($C_{1-6}$)alkyl, $C_{6-10}$ aryl($C_{1-6}$) alkoxy, hydroxy, $C_{1-6}$ alkylthio, $C_{1-6}$ alkylsulfinyl, $C_{1-6}$ alkylsulfonyl, $C_{6-10}$ arylthio, $C_{6-10}$ arylsulfinyl, $C_{6-10}$ arylsulfonyl, $C_{6-10}$ aryl, $C_{1-6}$ alkyl($C_{6-10}$)aryl, and halo($C_{6-10}$)aryl (e.g. where $R^2$ is —$CH_2$—$R^5$; $R^5$ is $C_6$ aryl; and $R^3$ is isobutyl); and
$Z^1$ and $Z^2$ are independently one of hydroxy, alkoxy, or aryloxy, or together $Z^1$ and $Z^2$ form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O (e.g., where $Z^1$ and $Z^2$ are hydroxyl and the compound is an ester salt). The compound may have inhibit proteasome activity and be effective for killing plasma cells. In preferred embodiments, the compound is N-(2-pyraxine)carbonyl-L-phenyla-lanine-L-leucine boronic acid, isomers thereof, stereoisomers thereof, purified enatiomers thereof, or pharmaceutically acceptable salts thereof.

Suitable proteasome inhibitors may include bortezomib (BZ) or pharmaceutically acceptable salts thereof (e.g., the drug sold under the tradename Velcade®, Millennium Pharmaceuticals, Inc.). The proteasome inhibitor may be administered at any effective dosage (e.g., at a dosage of about 0.7 mg/m² to about 1.9 mg/m²) and under any suitable regimen (e.g., no more than once a week for no more than about 4-8 weeks). For example, bortezomib may be administered at a dose of about 1.3 mg/m² once a week for about 4-8 doses.

In the disclosed methods, a proteasome inhibitor may be administered before, concurrently with, or after a GR agonist. The effects of proteasome inhibitors on GR expression and function have been studied. (See, e.g., Wallace et al., (2001) J Biol Chem 276(46):42714-42721; Kinyamu et al., (2003) Mol Cell Biol 23(16)5867-5881; and Kinyama et al., (2005) J Mol Endocrinol 34:281-297: the contents of which are incorporated herein by reference in their entireties). In some embodiments the methods include administering a "selective glucocorticoid receptor agonist (SEGRA)" otherwise referred to as a "dissociated glucocorticoid receptor agonist (DIGRA)". Regarding SEGRA, reference is made to Schäcke et al., "Insight into the molecular mechanisms of glucocorticoid receptor action promotes identification of novel ligands with an improved therapeutic index," Experimental Dermatology, 2006 15:565-573, the content of which is incorporated herein by reference in its entirety.

A "SEGRA" may be described as follows. In the absence of a GR agonist, the GR resides in the cytosol in an inactive state complexed with chaperone proteins (e.g., heat shock proteins (HSPs)). Binding of GR agonists to the GR activates the GR by causing dissociation of the bound chaperones. The activated GR can then regulate gene expression via one of two pathways. (See Rhen et al., (October 2005) N. Engl. J. Med. 353(16):1711-23, which is incorporated by reference herein in its entirety). One pathway of regulation is called "transactivation" whereby the activated GR dimerizes, is translocated into the nucleus and binds to specific sequences of DNA called GR response elements and forms a complex. The GR/DNA complex recruits other proteins which transcribe downstream DNA into mRNA and eventually protein. Examples of GR responsive genes include those that encode annexin A1, angiotensin-converting enzyme, neutral endopeptidase and other anti-inflammatory proteins. The other pathway of regulation is called "transrepression" in which activated monomeric GR binds to other transcription factors such as NF-κB and AP-1 and prevents these other factors from up-regulating the expression of their target genes. These target genes encode proteins such as cyclooxygenase, NO synthase, phospholipase A2, tumor necrosis factor, transforming growth factor beta. ICAM-1, MAP kinase phosphatase MKP1, serum and glucocorticoid-inducible protein kinase SGK, FK506-binding protein FKBP51 also called immunophilin, and a number of other pro-inflammatory proteins. (See Newton et al., (October 2007) Mol. Pharmacol 72(4):799-809, which is incorporated by reference herein in its entirety). As defined herein, a "SEGRA" selectively activates the GR such that the SEGRA more strongly transrepresses than transactivates. Suitable SEGRAs for the methods disclosed herein are known in the art and may include, but are not limited to BOL-303242-X, A 276575, RU 24858, and octahydrophenanthrene-2,7-diol derivatives. (See also Mealy et al., (2009) Drugs Fut 34 (4): 341; Robinson et al. (2009) Journal of medicinal chemistry 52 (6): 1731-43; Biggadike et al., (2007) Journal of Medicinal Chemistry 50 (26): 6519; Zhang et al. (2009) Molecular Vision 15: 2606-16; Vayssiére et al., (1997) Molecular Endocrinology 11 (9): 1245-55: Lin et al., (August 2002) Molecular Pharmacology 62 (2): 297-303; Schäcke et al., (January 2004) PNAS of the United States of America 101 (1): 227-32; Newton et al., (October 2007) Mol. Pharmacol. 72 (4): 799-809; Heinemann et al., (2008) Österreichische Apothekerzeitung 62 (23); Coghlan et al., (2003) Molecular Endocrinology 17 (5): 860; Reichardt et al., (May 1998) Cell 93 (4): 531-41; Reichardt et al., (2000) Biol. Chem. 381 (9-10): 961-4; Schäcke et al., (September 2007) Molecular and Cellular Endocrinology 275 (1-2): 109-17; Schäcke et al., (200)2) Ernst Schering Research Foundation workshop (40): 357-71; Renfro et al., (1992) Dermatologic Clinics 10 (3): 505-12; and Kerscher et al. (1995) International Journal of Clinical Pharmacology and Therapeutics 33 (4): 187-9; the contents of which are incorporated herein by reference in their entireties).

Suitable SEGRAs for the methods disclosed herein may include any of the following compounds or a combination thereof:

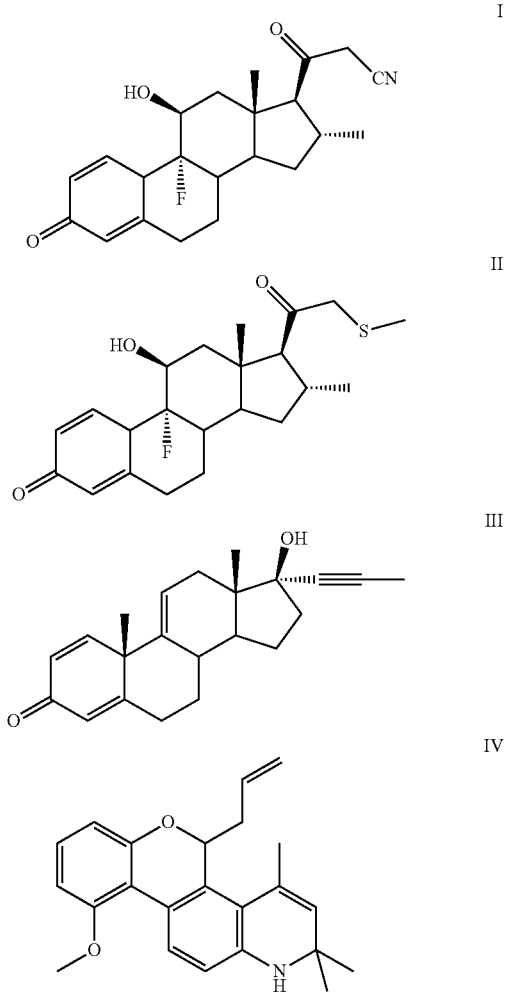

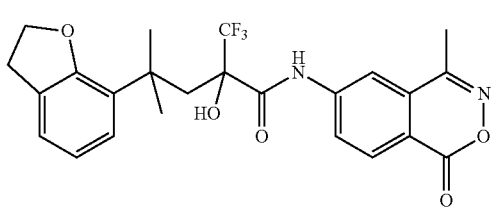

V

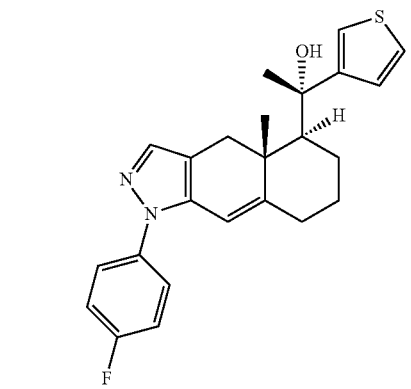

VI

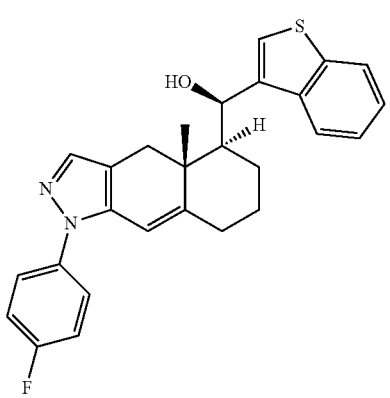

VII

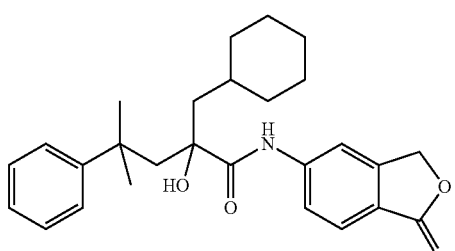

VIII

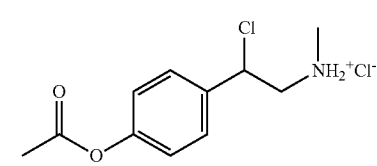

IX

The compounds utilized in the methods disclosed herein may be formulated as pharmaceutical compositions that include: (a) a therapeutically effective amount of one or more compounds as disclosed herein: and (b) one or more pharmaceutically acceptable carriers, excipients, or diluents. The pharmaceutical composition may include the compound in a range of about 0.1 to 2000) mg (preferably about 0.5 to 500 mg, and more preferably about 1 to 100 mg). The pharmaceutical composition may be administered to provide the compound at a daily dose of about 0.1 to 100 (mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21: dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules: solutions or suspensions in aqueous or non-aqueous liquids: edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base.

Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

EXAMPLES

The following Examples are illustrative and are not intended to limit the scope of the claimed subject matter.

The present inventors have observed that the proteasome inhibitor Bortezomib (BZ) recently approved by FDA for clinical use (treatment of blood cancers), strongly increases endogenous GR protein levels in human epithelial and lymphoid cell lines and in primary cell cultures. Moreover, treatment with BZ results in re-expression of GR in some glucocorticoid-resistant GR-negative cells. Further, GR protein expression can be increased both in the absence and in the presence of OR ligands such as glucocorticoids and SEGRA. Importantly, in the presence of GR ligands, cell pre-treatment with BZ results in the accumulation of GR whose function is defined by the ligand. For example, the present inventors have observed that in the presence of glucocorticoids, BZ induces the accumulation of GR that is proficient in both transactivation and transrepression. In the case of SEGRA, BZ induces the accumulation of GR whose activity is shifted towards transrepression. Thus, SEGRA+BZ administered in combination will maximize the anti-inflammatory and anti-proliferative effects of SEGRA therapy that are based on GR transrepression, and at the same time will not induce metabolic side effects typical for glucocorticoids that are based on GR transactivation.

Even though is known that proteasome inhibitors induce GR accumulation in cell cultures, the present inventors are unaware of any attempts to use proteasome inhibitors to increase patient sensitivity to glucocorticoids and to prevent development of tachyphylaxis. The present studies suggest that proteasome inhibitors could be used to increase GR levels in patient cells and hence increase their sensitivity to glucocorticoids. Moreover, in the presence of SEGRA that do not favor GR dimerization, proteasome inhibitors could be used to accumulate monomeric GR that has a better therapeutic index. Therefore the present inventors contemplate methods of treatment with proteasome inhibitor s such as BZ, to increase GR availability, prevent development of tachyphylaxis, and to modify GR function in a ligand-dependent fashion to provide maximally safe GR-targeted therapy for patients with inflammatory diseases and hyperproliferative disorders as well as for cancer patients.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of treating leukemia or myeloma comprising administering to a patient in need thereof a proteasome inhibitor and administering to the patient a glucocorticoid receptor (GR) agonist, wherein the proteasome inhibitor is administered before, concurrently with, or after the GR agonist is administered.

2. The method of claim 1, wherein the patient is administered an effective amount of the proteasome inhibitor for elevating GR levels in the patient.

3. The method of claim 1, wherein the patient has previously been administered a GR agonist and is exhibiting tachyphlaxis to GR agonist therapy.

4. The method of claim 1, wherein the patient has not previously been administered a OR agonist.

5. The method of claim 1, wherein the proteasome inhibitor is selected from a group consisting of peptide boronic acid compounds, NPI-0052, 2-pyrrolidone compounds, epigallocatechin 3-gallate (EGCG) analogs, PR-171, epoxomycin analogs, peptide analogs, tetrapeptide derivatives, tyropeptide A analogs, and combinations thereof.

6. The method of claim 5, wherein the proteasome inhibitor inhibits one or more enzymatic activities of a proteasome selected from β1 subunit activity, β2 subunit activity, and β5 subunit activity.

7. The method of claim 5, wherein the proteasome inhibitor is a peptide boronic acid compound that reversibly inhibits subunit β1 activity of the proteasome.

8. The method of claim 5, wherein the compound is bortezomib or a pharmaceutically acceptable salt thereof.

9. The method of claim 8, wherein the bortezomib is administered to the patient at a dosage of about 0.7 mg/m$^2$ to about 1.9 mg/m.

10. The method of claim 1, wherein the GR agonist is a selective GR agonist (SEGRA).

11. The method of claim 10, wherein the SEGRA is selected from a group consisting of (R-1,1,1-trifluoro-4-(5-fluoro-2,3-dihydrobenzofuran-7-yl)-4-methyl-2-{[(2-methyl-5-quinolyl)amino]methyl}pentan-2-ol) (BOL-303242-X), (2,5-dihydro-9-hydroxy-10-methoxy-2,2,4-trimethyl-5-(1-methylcyclohexen-3-yl)-1H-[1]benzopyrano[3,4-f]quinoline (A 276575U), and RU 24858 having a formula:

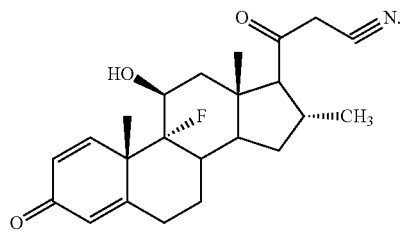

12. The method of claim 10, wherein the SEGRA is selected from the group of compounds consisting of

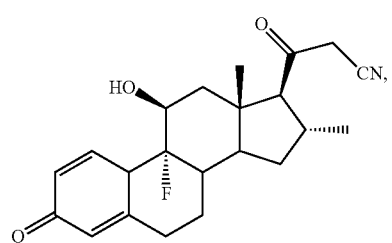

I

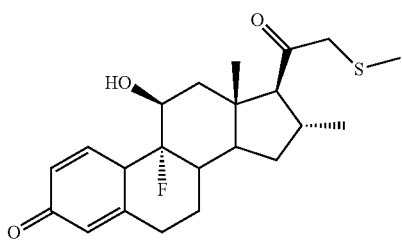

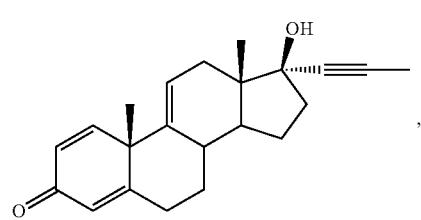

III

-continued

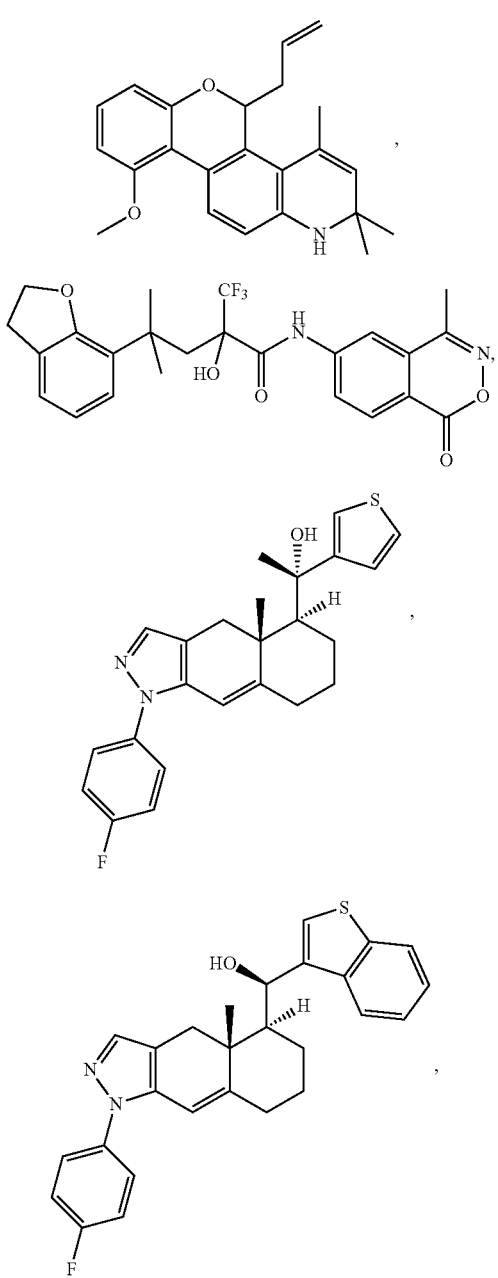

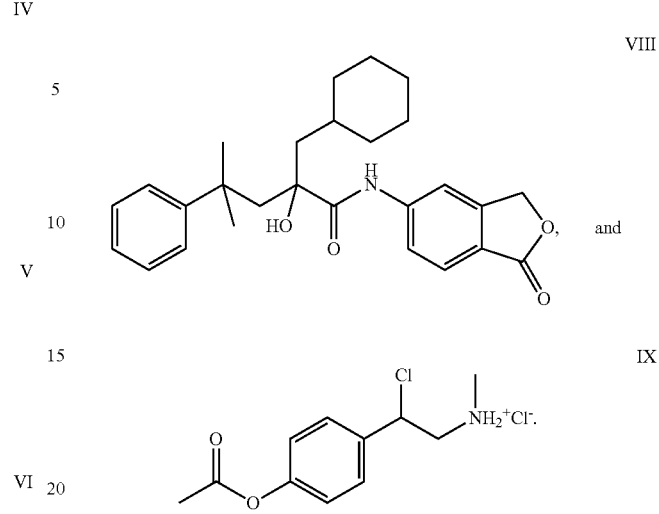

13. A method of treating myeloma comprising administering to a patient in need thereof a proteasome inhibitor and a selective GR agonist (SEGRA) to the patient.

14. The method of claim 13, wherein the proteasome inhibitor is bortezomib and the SEGRA is 2-(4-acetoxyphenyl)-2-chloro-N-methylethylammonium chloride.

15. The method of claim 13, wherein the proteasome inhibitor is administered before the GR agonist is administered.

16. The method of claim 13, wherein the proteasome inhibitor is administered concurrently with the GR agonist.

17. The method of claim 13, wherein the proteasome inhibitor is administered after the GR agonist is administered.

18. The method of claim 13, wherein the patient is administered an effective amount of the proteasome inhibitor for elevating GR levels in the patient.

19. The method of claim 13, wherein the patient has previously been administered a GR agonist and is exhibiting tachyphylaxis to GR agonist therapy.

20. The method of claim 13, wherein the patient has not previously been administered a GR agonist.

* * * * *